US012617754B2

(12) United States Patent
Beutner et al.

(10) Patent No.: US 12,617,754 B2
(45) Date of Patent: May 5, 2026

(54) PROCESS FOR SYNTHESIZING LIPIDS

(71) Applicant: Bristol-Myers Squibb Company, Princeton, NJ (US)

(72) Inventors: Gregory Louis Beutner, Princeton, NJ (US); Federico Lora Gonzalez, Princeton, NJ (US); Patricia Y. Cho, Princeton, NJ (US); Michael J. Smith, Princeton, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 611 days.

(21) Appl. No.: 18/003,228

(22) PCT Filed: Jun. 22, 2021

(86) PCT No.: PCT/US2021/038525

§ 371 (c)(1),
(2) Date: Dec. 23, 2022

(87) PCT Pub. No.: WO2021/262746

PCT Pub. Date: Dec. 30, 2021

(65) Prior Publication Data

US 2023/0250056 A1 Aug. 10, 2023

Related U.S. Application Data

(60) Provisional application No. 63/043,521, filed on Jun. 24, 2020.

(51) Int. Cl.
*C07C 323/41* (2006.01)
*C07C 319/14* (2006.01)

(52) U.S. Cl.
CPC .......... *C07C 323/41* (2013.01); *C07C 319/14* (2013.01)

(58) Field of Classification Search
CPC ............................ C07C 323/41; C07C 319/14
USPC .......................................................... 560/251
See application file for complete search history.

(56) References Cited

U.S. PATENT DOCUMENTS

2013/0017249 A1 1/2013 Niitsu et al.
2016/0074514 A1 3/2016 Payne et al.
2017/0022500 A1 1/2017 Minomi et al.
2018/0208547 A1 7/2018 Niitsu et al.
2018/0235995 A1 8/2018 Ying et al.

FOREIGN PATENT DOCUMENTS

JP S58203950 A 11/1983
JP H04112858 A 4/1992
WO 2012170952 A2 12/2012

OTHER PUBLICATIONS

International Search Report and Written Opinion for International Application No. PCT/US2021/038525, Mailed on Sep. 23, 2021, 5 pages.
International Preliminary Report on Patentability received for PCT Application No. PCT/US2021/038525, mailed on Sep. 23, 2021, 4 pages.
Beutner, G. L. et al. (Oct. 19, 2020). "Crystallizing Fats? Development of a Scalable, Chromatography-Free Synthesis of Cationic Lipids" Org. Process Res. Dev. 2020, 24, 2709-2721.

*Primary Examiner* — Ana Z Muresan
(74) *Attorney, Agent, or Firm* — Mintz, Levin, Cohn, Ferris, Glovsky and Popeo, P.C

(57) ABSTRACT

The present application provides processes for synthesizing lipids of Formula I useful in the synthesis of fat-soluble compounds for targeting and enhancing activity of therapeutic molecules, including siRNA.

Formula I

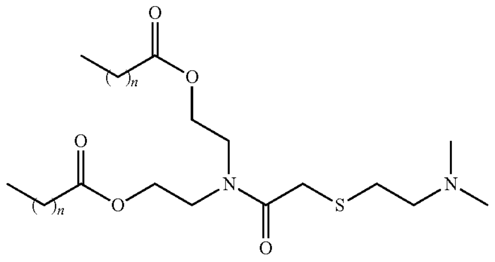

16 Claims, No Drawings

PROCESS FOR SYNTHESIZING LIPIDS

CROSS-REFERENCE TO RELATED APPLICATIONS

This application is a U.S. National Phase Application under 35 U.S.C. § 371 of International Patent Application Number PCT/US2021/038525, filed Jun. 22, 2021, which claims the benefit of U.S. Provisional Application 63/043,521 filed Jun. 24, 2020, each of which is incorporated herein by reference in its entirety for all purposes.

FIELD OF THE INVENTION

The present application provides processes for synthesizing lipids useful in the synthesis of fat-soluble compounds for targeting and enhancing activity of therapeutic molecules, including siRNA.

BACKGROUND OF THE INVENTION

A number of techniques are available for delivering a therapeutic agent such as siRNA into a cell, including the use of viral transfection systems and non-viral transfection systems. Non-viral transfection systems can include, for example, polymers, lipids, liposomes, micelles, dendrimers, and nano materials. Examples of polymers that have previously been studied for cell transfection include cationic polymers such as poly(L-lysine) (PLL), polyethyleneimine (PEI), chitosan, and poly(2-dimethylamino)ethyl methacrylate (pD MAEMA). Each type of system has its respective advantages and drawbacks. For example, viral systems can yield high transfection efficiency, but may not be as safe as some non-viral systems. In addition, viral systems can be complicated and/or expensive to prepare. Non-viral transfection systems, such as cationic polymers and/or lipids, have been reported to transfer plasmid DNA into cells. Cationic lipids possess a number of advantages.

One such example of a cationic lipid is ((2-((2-(dimethylamino)ethyl)thio)acetyl)azanediyl)bis(ethane-2,1-diyl) ditetradecanoate (S104), as disclosed in U.S. Pat. No. 8,308,267. Previous synthetic strategies for producing S104 and similar compounds were plagued with low yield, inconvenient work-up procedures, and a high number of side products.

There remains a need for a synthetic process to produce these cationic lipids that facilitates increased product yield, low by-product yield, and uses more accessible synthetic techniques.

SUMMARY OF THE INVENTION

In one aspect, the present application provides a process for producing S104.

In one embodiment the present application provides a process for synthesizing a compound of Formula I

I

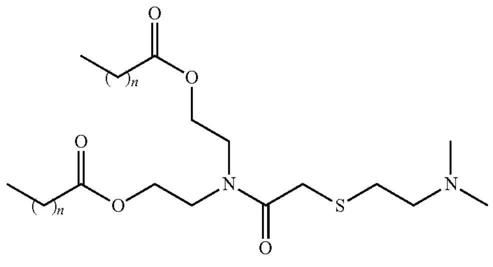

wherein n is an integer from 8-16 the process comprising, a) reacting a compound of Formula II

II

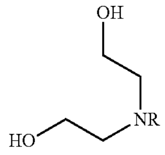

wherein R is a protecting group;

with a compound of Formula III

III

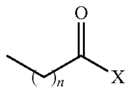

wherein X is a halogen;

followed by treatment with methane sulfonic acid, to form a compound of Formula IV;

IV

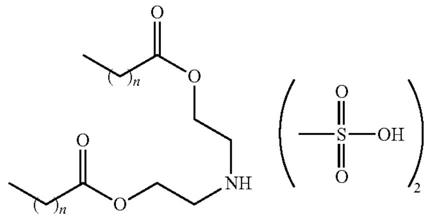

b) reacting a compound of Formula IV under coupling conditions with a compound of Formula V

V

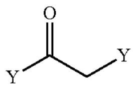

wherein each Y is independently a halogen;

to form a compound of Formula VI;

VI

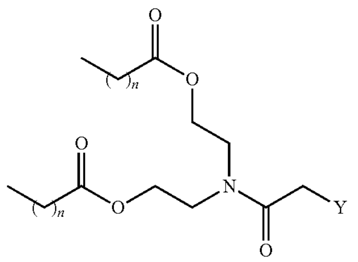

c) reacting a compound of Formula VI under coupling conditions with 2-(dimethylamino)ethanethiol HCl, followed by treatment with oxalic acid, to form a compound of Formula VII;

VII

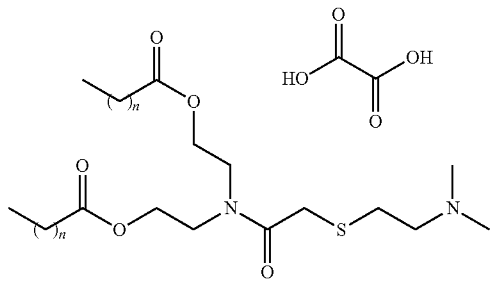

and d) reacting the compound of Formula VII with a base to produce a compound of Formula I.

In an embodiment the coupling conditions of step b) comprise reacting a compound of Formula IV with a base. In an embodiment the base is trimethylamine.

In an embodiment the coupling conditions of step c) comprise reacting a compound of Formula VI with a base. In an embodiment the base is trimethylamine.

In another further embodiment n is 12.

In another embodiment R is independently selected from the group consisting of carboxybenzyl, p-methoxybenzyl carbonyl, t-butyloxycarbonyl, 9-fluorenylmetholoxycarbonyl, acetyl, trifluoroacetyl, benzoyl, benzyl, carbamate, p-methoxybenzyl, 3,4-dimethoxybenzyl, p-methoxybenzyl, tosyl, trichloroethyl chloroformate, (4-nitrophenyl)sulfonyl, methyl, ethyl, propyl, n-butyl, t-butyl, succinimide, 2,6-dimethylphenol, 2,6-diisopropylphenol, 2,6-di-tert-butylphenol, trimethylsilyl, allyl, 1,1-dimethylallyl, 2,2,2-trifluoro ethyl, phenyl, and 4-methoxybenzyl.

In a further embodiment R is t-butyloxycarbonyl.

In another embodiment each Y is independently selected from Cl, Br, and I. In another embodiment each Y is the same. In a further embodiment each Y is Cl.

In another embodiment X is independently selected from Cl, Br, and I. In a further embodiment X is Cl.

In a further embodiment the compound of Formula VI is

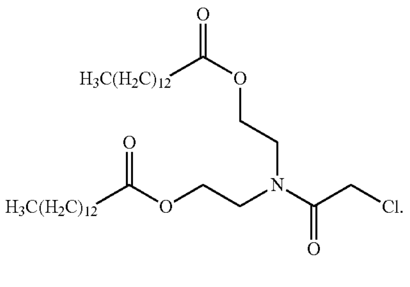

In a further embodiment the yield of step a) is at least about 75%.

In a further embodiment the compound of Formula I is

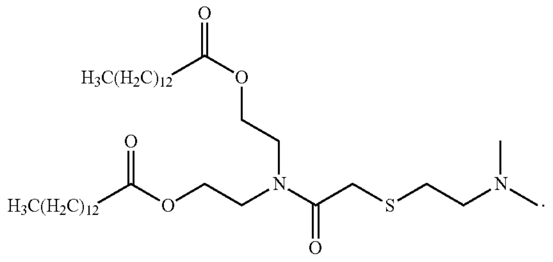

In a further embodiment the compound of Formula I is produced in at least about 70% yield from the compound of Formula II.

In a further embodiment a compound VIII

VIII

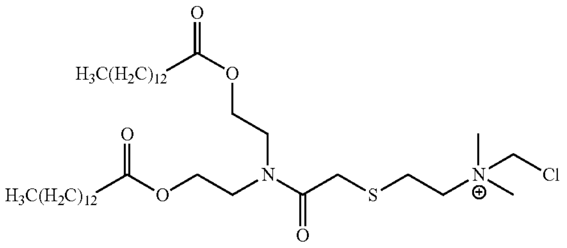

is present in the product from step d) in a concentration of less than 500 ppm.

In a further embodiment compound VIII is present in the product from step d) in a concentration of less than 100 ppm.

In a further embodiment the compound of Formula VII is isolated as a solid. In a further embodiment the compound of Formula VII is isolated as a crystalline solid.

In an embodiment the purity of the produced compound of Formula VII is between about 95% and 99.9% by liquid chromatography area percent (LCAP) with no chromatography purification.

In a further embodiment the compound of Formula VI is not isolated.

In another embodiment a compound of Formula I is prepared by the process of steps a)-d).

DETAILED DESCRIPTION OF THE INVENTION

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C═C double bonds, C═N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity. It is well understood in the art that controlling the stereochemistry of a product is possible by choosing the stereochemistry of the starting materials, and that the stereochemistry of a product can be changed by changing the stereochemistry of the starting material. It is also well understood in the art how to separate a racemic mixture such that the stereochemical purity of a product is >99%.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, Pure and Applied Chemistry, 68, 2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

The term "LCAP" refers to liquid chromatography area percentage as collected on Waters Acquity HPLC.

Abbreviations as used herein, are defined as follows: "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "conc." for concentrate, "sat" or "saturated" for saturated, "MW" for molecular weight, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "NMR" for nuclear magnetic resonance spectroscopy, "$^1$H" for proton, and "D", "L" "α", "β", "R", "S", "E", and "Z" are stereochemical designations familiar to one skilled in the art.

Step a)

In an embodiment step a) comprises reacting a compound of Formula II

II

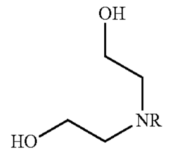

wherein R is a protecting group;
with a compound of Formula III

III

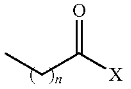

wherein, n is an integer from 8-16; and
X is a halogen;
followed by treatment with methanesulfonic acid, to form a compound of Formula IV

IV

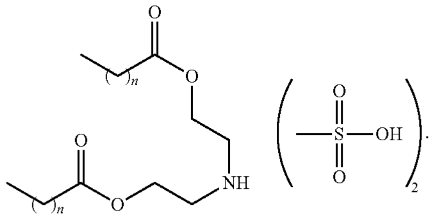

In an embodiment R is an amine protecting group. In another embodiment R is selected from the group consisting of carboxybenzyl), p-methoxybenzyl carbonyl, t-butyloxycarbonyl, 9-fluorenylmetholoxycarbonyl, Acetyl, trifluoroacetyl, benzoyl, benzyl, carbamate, p-methoxybenzyl, 3,4-dimethoxybenzyl, p-methoxybenzyl, tosyl, trichloroethyl chloroformate, (4-nitrophenyl)sulfonyl. In an embodiment R is t-butyloxycarbonyl.

In an embodiment n is an integer 8-16. In another embodiment n is an integer 8-9, 8-10, 8-11, 8-12, or 8-13. In an embodiment n is an integer 10-14. In another embodiment n is an integer 2-10, 3-10, 4-10, 5-10, 6-10, 7-10, 8-10, or 9-10. In another embodiment n is an integer 9-13 or 10-12. In an embodiment n is 8. In an embodiment n is 9. In an embodiment n is 10. In an embodiment n is 11. In an embodiment n is 12. In an embodiment n is 13. In an embodiment n is 14.

In an embodiment X is a halogen. In another embodiment X is selected from the group consisting of fluorine (F), chlorine (Cl), bromine (Br), iodine (I), and astatine (At). In a further embodiment X is F. In a further embodiment X is Cl. In a further embodiment X is Br. In a further embodiment X is I.

In an embodiment step a) takes place in a solvent. In an embodiment step a) takes place in a mixture of solvents. In an embodiment at least one solvent is non-polar. In an embodiment the solvent(s) is selected from pentane, hexane, cyclohexane, benzene, toluene, chloroform, diethyl ether, heptane, MTBE, and cyclopropyl methyl ether. In an embodiment step b) takes place in toluene.

In an embodiment the compound of Formula IV is isolated as a crystalline solid. In an embodiment step a) does not require chromatography for isolation or purification.

In an embodiment the compound of Formula IV is isolated as a crystalline solid. In an embodiment step a) does not require chromatography for isolation or purification. In an embodiment the purity of the produced compound of Formula IV is between about 95% and 99.9% by liquid chromatography area percent (LCAP) with no chromatography purification. In an embodiment the purity of the produced compound of Formula IV is at least about 95% by LCAP with no chromatography purification.

In an embodiment the crystalline compound of Formula IV is produced in between about 70% and 95% yield from step a). In an embodiment the compound of Formula IV is produced, in between about 70% and 85%, or in between about 70% and 75% yield. In another embodiment the compound of Formula IV is produced in between about 80% and about 95%, or in between about 90% and 95% yield. In another embodiment the compound of Formula IV is produced in about 70%, about 75%, about 80%, about 85%, about 90%, or about 95% yield. In a further embodiment the compound of Formula IV is produced in about 80% yield. In an embodiment the compound of Formula IV is produced in at least about 65% yield, in at least 70% yield, in at least 75% yield, in at least about 80% yield, or at least about 85% yield from step a). In another embodiment Formula IV is produced in at least about 80% yield from step a).

In an embodiment step a) is a two-step process. The first reaction is a N-methyl-morpholine-catalyzed double myristoylation of a compound of Formula I. Upon reaction completion, the mixture is washed with 1N aqueous acetic acid to remove unreacted starting material and salts, followed by a drying distillation. The second reaction is a N-Boc-deprotection reaction and subsequent salt formation with methanesulfonic acid (MSA).

Step b

In an embodiment step b comprises reacting a compound of Formula IV with a compound of Formula V

V

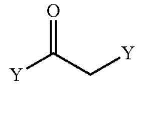

wherein each Y is independently a halogen;
to form a compound of Formula VI

VI

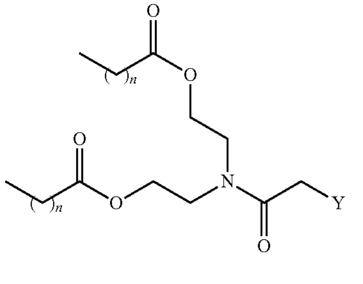

In an embodiment n is as described for step a). In an embodiment n is 12.

In an embodiment step b) takes place in a solvent. In an embodiment at least one solvent is polar aprotic. In an embodiment the solvent(s) is selected from dichloromethane (DCM), ethyl acetate (EtOAc), tetrahydrofuran (THF), acetone, N,N-dimethylformamide (DMF), acetonitrile, and dimethyl sulfoxide (DMSO). In an embodiment step b) takes place in EtOAc.

In an embodiment step c) comprises reacting a compound of Formula V with a base. In an embodiment the base is a tertiary amine. In an embodiment the base is selected from trimethylamine, DIPEA, N-methylmorpholine, sodium hydroxide, and potassium hydroxide. In an embodiment the base is trimethylamine.

In an embodiment step b) takes place between about 0° C. and about 30° C. In an embodiment the process takes places between about 10° C. and about 30° C., or between about 20° C. and about 30° C. In an embodiment step b) takes place between about 0° C. and about 25° C. between about 0° C. and about 15° C., or between about 0° C. and about 5° C. In an embodiment step b) takes place between about 15° C. and about 20° C. In an embodiment step b) takes place at about 30° C., about 25° C., about 20° C., about 15° C., about 10° C., about 5° C., or about 0° C. In an embodiment step b) takes place at less than about 30° C. In an embodiment step b) takes place at less than about 25° C. In an embodiment step b) takes place at about 20° C. In an embodiment step b) takes place at about room temperature.

In an embodiment step b) further comprises two aqueous washes (aqueous acetic acid and $KHCO_3/K_2CO_3$/brine, respectively) to remove unreacted reagents and organic salt byproducts.

In an embodiment the compound of Formula VI is not isolated. In an embodiment step b) is s a chloroacetylation of a compound of Formula IV.

Step c

In an embodiment step c) comprises reacting a compound of Formula VI under coupling conditions with 2-(dimethylamino)ethanethiol HCl, followed by treatment with oxalic acid, to form a compound of Formula VII

VII

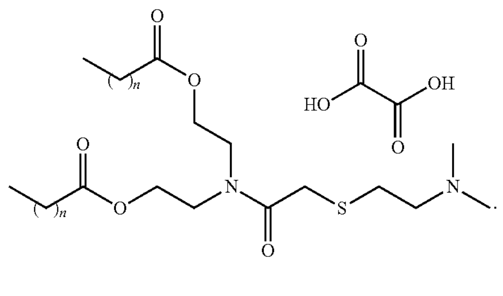

In an embodiment n is described in step a). In an embodiment n is 12.

In an embodiment step c) takes place in a solvent. In an embodiment the solvent is a combination of solvents. In another embodiment at least one solvent is polar protic. In another embodiment at least one solvent is polar aprotic. In another embodiment at least one solvent is polar protic. In another embodiment the solvent(s) is selected from the group consisting of dichloromethane, N-methylpyrrolidone, tetrahydrofuran, ethyl acetate, acetone, dimethylformamide, acetonitrile, dimethyl sulfoxide, ethanol, methanol, acetic acid, and water. In an embodiment step c) takes place in a combination of acetonitrile and water.

In an embodiment the coupling conditions comprise a base. In an embodiment the base is a tertiary amine. In an embodiment the base is selected from trimethylamine, sodium hydroxide, DIPEA, N-methylmorpholine, and potassium hydroxide. In an embodiment the base is trimethylamine.

In an embodiment step c) takes place between about 0° C. and about 30° C. In an embodiment the process takes places between about 10° C. and about 30° C., or between about 20° C. and about 30° C. In an embodiment step c) takes place between about 0° C. and about 25° C. between about 0° C. and about 15° C., or between about 0° C. and about 5° C. In an embodiment step c) takes place between about 15° C. and about 25° C. In an embodiment step c) takes place at about 30° C., about 25° C., about 20° C., about 15° C., about 10° C., about 5° C., or about 0° C. In an embodiment step c) takes place at less than about 30° C. In an embodiment step c) takes place at about 25° C.

In an embodiment step c) further comprises two aqueous washes (aqueous acetic acid/brine and $KHCO_3/K_2CO_3/$ brine, respectively) before treatment with oxalic acid, which removes unreacted reagents and organic salt byproducts.

In an embodiment the compound of Formula VII is isolated as a crystalline solid. In an embodiment step c) does not require chromatography for isolation or purification. In an embodiment the purity of the produced compound of Formula VII is between about 95% and 99.9% by LCAP with no chromatography purification. In an embodiment the purity of the produced compound of Formula VII is about 99% by LCAP with no chromatography purification. In an embodiment the purity of the produced compound of Formula VII is at least about 95% by LCAP with no chromatography purification.

In an embodiment the crystalline compound of Formula VII is produced in between about 70% and 95% yield from step c). In an embodiment the compound of Formula VII is produced, in between about 70% and 85%, or in between about 70% and 75% yield. In another embodiment the compound of Formula VII is produced in between about 80% and about 95%, or in between about 90% and 95% yield. In another embodiment the compound of Formula VII is produced in about 70%, about 75%, about 80%, about 85%, about 90%, or about 95% yield. In a further embodiment the compound of Formula VII is produced in about 80% yield. In an embodiment the compound of Formula VII is produced in at least about 65% yield, in at least 70% yield, in at least 75% yield, in at least about 80% yield, or at least about 85% yield from step c). In another embodiment Formula VII is produced in at least about 80% yield from step c).

In an embodiment step c) is a coupling reaction. In an embodiment step c) is a coupling of 2-(dimethylamino) ethanethiol HCl with a compound of Formula VI via C—S bond formation followed by oxalate salt formation.

Step d

In an embodiment step d) comprises reacting a compound of Formula VII with a base to form a compound of Formula I.

In an embodiment the crystalline compound of Formula I is produced in between about 70% and 95% yield from step d). In an embodiment the compound of Formula VII is produced, in between about 70% and 85%, or in between about 70% and 75% yield. In another embodiment the compound of Formula VII is produced in between about 80% and about 95%, or in between about 90% and 95% yield. In another embodiment the compound of Formula VII is produced in about 70%, about 75%, about 80%, about 85%, about 90%, or about 95% yield. In a further embodiment the compound of Formula VII is produced in about 80% yield. In an embodiment the compound of Formula VII is produced in at least about 65% yield, in at least 70% yield, in at least 75% yield, in at least about 80% yield, or at least about 85% yield from step d). In another embodiment Formula VII is produced in at least about 80% yield from step d).

In a further embodiment a compound VIII

VIII

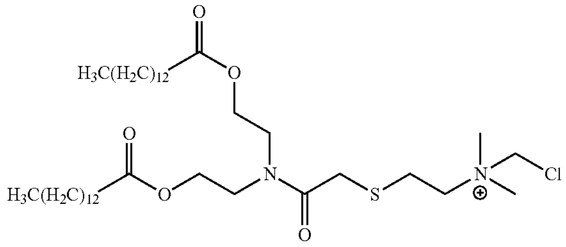

is present in the product from step d) in a concentration of less than about 500 ppm. This by-product was a contributing factor in the previous synthetic route's level of genotoxic impurities (GTI).

In another embodiment compound VIII is present in the product from step d) in a concentration of less than less than about 300 ppm. In another embodiment compound VIII is present in the product from step d) in a concentration of less than less than about 200 ppm. In another embodiment compound VIII is present in the product from step d) in a concentration of less than less than about 100 ppm. In another embodiment compound VIII is present in the product from step d) in a concentration of less than about 50 ppm. In a further embodiment compound VIII is not produced in the process.

Overall Process

In an embodiment the compound of Formula I is produced in between about 40% and about 80% overall yield from the compound of Formula II. In an embodiment the compound of Formula I is produced in between about 40% and about 70% yield, about 40% and about 60% yield, about 40% and about 50% yield, or about 40% and about 45% yield from the compound of Formula III. In an embodiment the compound of Formula I is produced in between about 50% and about 80%, about 60% and about 80% yield, about 70% and about 80% yield, about 75% and about 80% yield, about 80% and about 80% yield, or about 85% and about 80% yield from the compound of Formula II. In an embodiment the compound of Formula I is produced in about 55% yield from the compound of Formula II. In an embodiment the compound of Formula I is produced in about 60% yield from the compound of Formula II.

In an embodiment the compound of Formula I is produced in at least about 40% yield, at least about 50% yield, at least about 60% yield, or at least about 65% yield from the compound of Formula II. In an embodiment the compound of Formula I is produced in at least about 50% yield from the compound of Formula II. In an embodiment the compound of Formula I is produced in at least about 60% yield from the compound of Formula II. In an embodiment the compound of Formula I is produced in at least about 65% yield from the compound of Formula II.

EXAMPLES

Example 1. Synthesis of azanediylbis(ethane-2,1-diyl) ditetradecanoate methanesulfonic acid salt methanesulfonic acid solvate

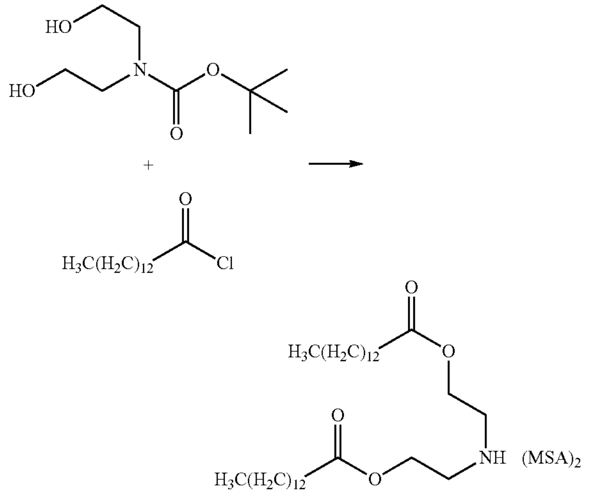

Toluene (26.1 kg, 30.0 L, 30 L/kg) was charged to Reactor 1 followed by N-Boc-diethanolamine (1.00 kg, 0.920 L). Observation: The presence of water can lead to the myristoylation reaction stalling and higher levels of an impurity (myristic acid). Reactor should be rinsed and dried thoroughly prior to use. The jacket temperature was set to 15-25° C. (target 20° C.). N-methyl-morpholine (1.68 kg, 1.82 L, 3.4 equiv) was charged. Myristoyl chloride (2.65 kg, 2.94 L, 2.2 equiv) was charged to the reactor over no less than 30 minutes, maintaining a batch temperature <30° C. (target 20° C.). The reaction was aged at 15-25° C. (target 20° C.) for no less than 5 hours.

Acetic acid 1N in half brine (11.0 kg, 10 L, 10 L/kg) was charged to the reactor. The reaction was heated to 25-35° C. (target 30° C.) under agitation and aged for 30 minutes. Agitation was stopped and the reaction was allowed to settle the phases for at least 30 minutes. The phases were split, sending the aqueous bottom phase to waste. This wash was repeated.

The organic layer was distilled under vacuum (P<100 mbar) to a final volume of 14 L/kg maintaining a jacket setpoint temperature 45° C. Observation: The distillation is typically performed as a put and take, a minimum volume of 20 L/kg of toluene added is recommended to dry the stream. The presence of water in the subsequent steps can lead to the decomposition of the product. These impurities significantly increase the solubility of the product, which in turn significantly decreases yield. Additionally, changes in the solubility affect the seed point in step 28.

The reaction mixture was transferred to Reactor 2 through a polish filter, to remove precipitated NaCl. Toluene was charged as a vessel rinse of Reactor 1 using a sprayball and transferred through the polish filter line to Reactor 2 (3.48 kg, 4.0 L, 4.0 L/kg). The reaction was heated to 30-40° C. (target 35° C.) under agitation and nitrogen atmosphere. Methanesulfonic acid (0.936 kg, 0.693 L, 2.0 equiv.) was charged over no less than 30 minutes, maintaining a batch temperature 30-40° C. (target 35° C.). Note: Use anhydrous methanesulfonic acid (KF<0.75 wt %). Excess water can cause decomposition of product. Anhydrous ethyl acetate (2.70 kg, 3.0 L, 3.0 L/kg) was charged to the reaction and the reaction was aged at 30-40° C. (target 35° C.) for no less than 1 hour then cooled to 27-31° C. (target 29° C.).

Azanediylbis(ethane-2,1-diyl) ditetradecanoate methanesulfonic acid salt methanesulfonic acid solvate seeds (0.050 kg, 5 wt %) were charged to the reaction. The reaction was then cooled to 10-20° C. (target 15° C.) over no less than five hours.

The following cool down ramp was implemented:

i. 29° C. to 27.25° C. over 30% of the total cool down time
ii. 27.25° C. to 24.5° C. over 30% of the total cool down time
iii. 24.5° C. to 15° C. over 40% of the total cool down time Observation: A non-linear cool down is implemented to aid in filtration rate and impurity purge, due to the impact of temperature on the solubility of the product in toluene/ethyl acetate.

The reaction batch was then cooled at 10-20° C. (target 15° C.) for 1 hour and filtered. Tertiary-butyl methyl ether (MTBE, 2.22 kg, 3.0 L, 3.0 L/kg) was charged to reactor 1 as a crystallizer flush and cooled to 10-20° C. (target 15° C.). The product cake was then rinsed with the MTBE wash from reactor 1, filtering the wash. The cake was dried under vacuum and nitrogen sweep, at a jacket setpoint of 20-30° C. (target 25° C.) to yield crystalline azanediylbis(ethane-2,1-diyl) ditetradecanoate methanesulfonic acid salt methanesulfonic acid solvate in 90% yield. Observation: Elevated temperatures can cause the wet cake to melt/dissolve and lead to significant degradation of the product.

Example 2. Synthesis of ((2-chloroacetyl)azanediyl)bis(ethane-2,1-diyl) ditetradecanoate

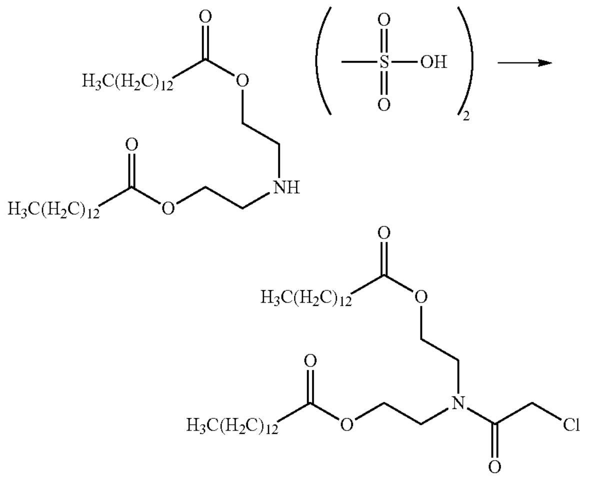

Azanediylbis(ethane-2,1-diyl) ditetradecanoate methanesulfonic acid salt methanesulfonic acid solvate (1 kg, 1 equiv.) was charged to Reactor 3 followed by EtOAc (10 L, 10.0 L/kg). Triethylamine (0.457 kg, 3.25 equiv.) was added. Chloroacetyl chloride (0.213 kg, 1.36 equiv.) was then added to Reactor 3. Note: Charge is exothermic. Charge slowly while maintaining the batch temperature below 25° C. The reaction was aged for at least 1 h at 20° C.

Upon reaction completion water (9.68 L, 9.68 L/kg) was charged to Reactor 3 followed by acetic acid glacial (0.29 L, 0.29 L/kg) and settled without agitation for at least 0.5 h at 25° C. Observation: The acidic aqueous buffer will remove unreacted reagents and reaction by-products. Age for at least 0.5 h at 25° C. The phase were then separated, sending the lower aqueous layer to waste.

The organic layer was agitated and pH 9.5 carbonate buffer solution (10 L, 10 L/kg) was added. The reaction aged at least 0.5 h at 25° C. Agitation was stopped and the reaction was allowed to settle for at least 0.5 h at 25° C. The phases were then separated, sending the lower aqueous layer from Reactor 3 to waste.

Example 3. Synthesis of Synthesis of ((2-((2-(dimethylamino)ethyl)thio)acetyl)azanediyl)bis(ethane-2,1-diyl) ditetradecanoate oxalate salt

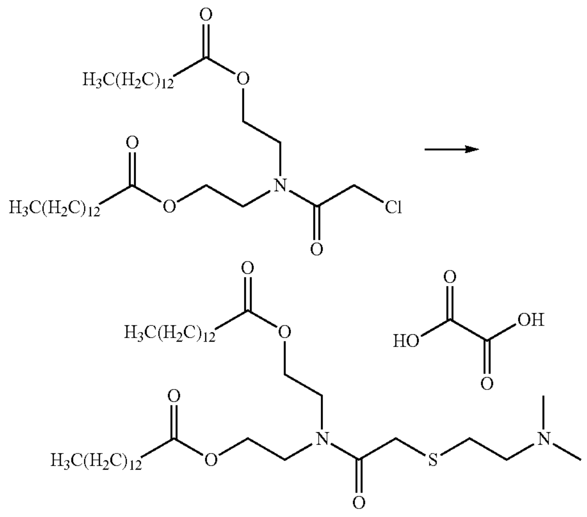

2-(dimethylamino)ethanethiol HCl (0.375 kg, 1.90 equiv.) was charged to Reactor 4 followed by acetonitrile (10 L, 10.0 L/kg). Water (0.16 L, 0.16 L/kg) was added and the reaction aged for at least 0.5 h at 25° C. Note: visual confirmation of complete dissolution is required. If not, impurity will form at higher than typical level that does not purge.

Triethylamine (0.538 kg, 3.82 equiv.) was charged to Reactor 3. Reaction mixture from Reactor 3 was transferred to Reactor 4 over no less than 2 h, and aged for no less than an additional 3 h. Note: The ((2-chloroacetyl)azanediyl)bis(ethane-2,1-diyl) ditetradecanoate stream is charged slowly to maintain the relative concentration of 2-(dimethylamino)ethanethiol to ((2-chloroacetyl)azanediyl)bis(ethane-2,1-diyl) ditetradecanoate in solution high, to minimize the formation of impurity.

Water (8.03 L, 8.03 L/kg) was charged to Reactor 4 followed by acetic acid glacial (0.29 L, 0.29 L/kg). Sodium chloride brine 25% (1.68 L, 1.68 L/kg) was added and the reaction aged for at least 0.5 h at 25° C. Agitation was stopped and the reaction was allowed to settle for at least 0.5 h at 25° C. The phases were separated, sending the lower aqueous layer from Reactor 4 to waste.

The remaining organic layer was agitated and pH 9.5 carbonate buffer solution (10 L, 10 L/kg) was added. The reaction aged for at least 0.5 h at 25° C. Agitation was stopped and the reaction was allowed to settle for at least 0.5 h at 25° C. The phases were separated, sending the lower aqueous layer from Reactor 4 to waste.

The organic layer was distilled at a pressure of 150 mbar or lower with max-imum batch temperature of 30° C. batch to 5 L (Target is 5 L/kg). Toluene was charged (10 L, 10.0 L/kg) and the reaction was concentrated by distillation performed at a pressure of 75 mbar or lower with maxi-mum batch temperature of 30° C. to 5 L. Toluene (2.5 L, 2.5 L/kg) was charged.

EtOAc (12.5 L, 12.5 L/kg) was charged to Reactor 4 and the reaction was heated to 38° C. Oxalic acid solution (5 L, 5.0 L/kg, 1.14 equiv) was then added over at least 2 h. Note: Charge oxalic acid solution at an approximately constant rate over the addition time. If the addition rate changes drastically (i.e. slow addition followed by fast addition), the batch may become too supersaturated, and there is a risk of secondary nucleation. The reaction was then cooled to 20° C. over 2 h and aged for 1 h. The resultant slurry was filtered. Reactor 4 was then rinsed with EtOAc (5 L, 5.0 L/kg). The rinse was used to wash product cake. The product cake was dried at a jacket setpoint temperature of ≤40° C. under vacuum to yield ((2-((2-(dimethylamino)ethyl)thio)acetyl)azanediyl)bis(ethane-2,1-diyl) ditetradecanoate oxalate salt at 83% yield from azanediylbis(ethane-2,1-diyl) ditetradecanoate methanesulfonic acid salt methanesulfonic acid solvate.

Example 4. Synthesis of ((2-((2-(dimethylamino)ethyl)thio)acetyl)azanediyl)bis(ethane-2,1-diyl) ditetradecanoate

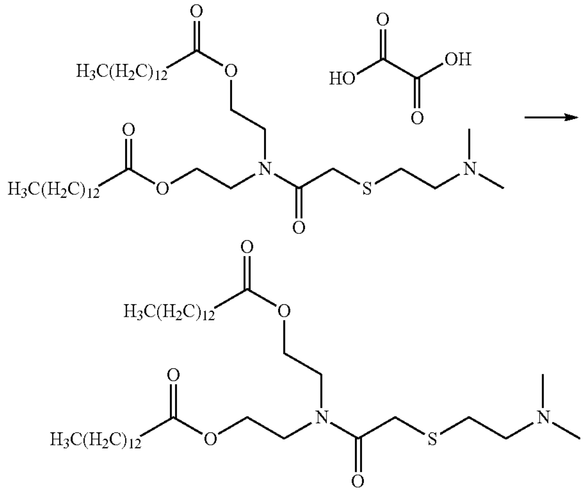

EtOAc (20 L) was charged to Reactor 1 followed by ((2-((2-(dimethylamino)ethyl)thio)acetyl)azanediyl)bis(ethane-2,1-diyl) ditetradecanoate oxalate salt (1 kg). pH 9.5 carbonate buffer solution (15 L) was then charged to Reactor 1. The solution was heated to 25° C., then aged for at least 0.5 h. Agitation stopped and allow to settle for at least 0.5 h at 20° C. Separated the phases, sending the lower aqueous layer from Reactor 1 to waste. Water (8.32 L) was then to Reactor 1 followed by Sodium Chloride Brine 25% (1.75 L) Solution was aged for at least 0.5 h at 25° C. Agitation stopped and allow to settle for at least 0.5 h at 25° C. Phases were separated, sending the lower aqueous layer to waste.

Product phase was concentrated to 10 L (target is 10 L/kg). Distillation performed at a pressure of 150 mbar with a maximum batch temperature <30° C. The product may degrade at high temperature in the presence of water. EtOAc was charged (6 L) to Reactor 1 and concentrated to 10 L (target is 10 L/kg). Distillation should be performed at a pressure of 150 mbar with a maximum batch temperature <30° C. The product may degrade at high temperature in the presence of water. EtOAc was charged (6 L) to Reactor 1 then concentrated to 5 L (target is 5 L/kg). Distillation should be performed at a pressure of 150 mbar with a maximum batch temperature <30° C. The product may degrade at high temperature in the presence of water.

The product was then polish filtered from Reactor 1 to Reactor 2. A solvent swap into MeCN via distillation was done. Distillation should be performed at a pressure of 150 mbar with a maximum batch temperature <30° C. MeCN (13 L/kg) was charged to Reactor 2 at 25° C. Reactor 2 cooled to 23±0.5° C. Product was charged (0.005 kg) to Reactor 2 and aged for at least 1 h at 23° C. The following cooling gradient was done:

Reactor 2 to 20° C. over 2 h.

Reactor 2 to 10° C. over 2.5 h

Reactor 2 to 0° C. over 1.5 h

Reactor 2 to −10° C. over 1 h.

It is critical to control the temperature ramp tightly to prevent uncontrolled nucleation on reactor wall, which results in product loss on reactor walls. The product was aged for at least 1 h at −10° C. The slurry was then transferred and filtered. The cake wash was cooled in Reactor 2 to −10° C. under agitation then transferred to the filter to wash cake The cake was dried at a temperature of ≤25° C. under vacuum to yield ((2-((2-(dimethylamino) ethyl)thio)acetyl)azanediyl)bis(ethane-2,1-diyl) ditetradecanoate in 93% yield.

What is claimed is:

1. A process for synthesizing a compound of Formula I:

I

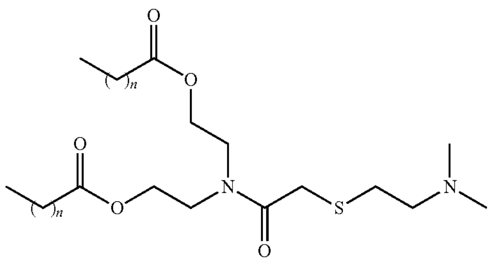

wherein n is an integer from 8-16, the process comprising, a) reacting in a first solvent a compound of Formula II:

II

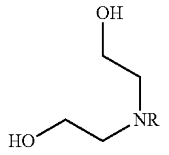

wherein R is a protecting group;

with a compound of Formula III

III

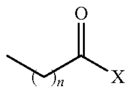

wherein n is an integer from 8-16, and X is a halogen;

followed by treatment with methane sulfonic acid, to form a compound of Formula IV:

IV

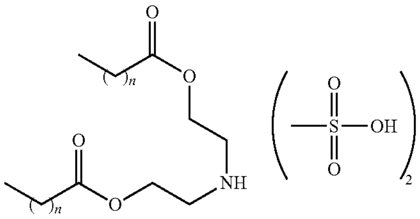

b) reacting in a second solvent a compound of Formula IV with a first base and a compound of Formula V:

V

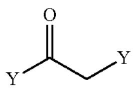

wherein each Y is independently a halogen;

to form a compound of Formula VI:

VI

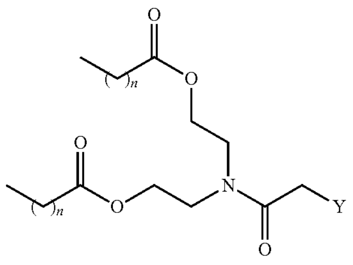

c) reacting in a third solvent a compound of Formula VI under coupling conditions with a second base and 2-(dimethylamino) ethanethiol HCl, followed by treatment with oxalic acid, to form a compound of Formula VII:

VII

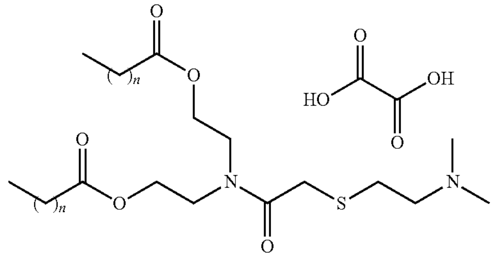

and d) reacting a compound of Formula VII with a third base to produce a compound of Formula I.

2. The process of claim 1, wherein the first base is triethylamine.

3. The process of claim 1, wherein the second base is triethylamine.

4. The process of claim 1, wherein n is 12.

5. The process of claim 1, wherein R is selected from the group consisting of carboxybenzyl, p-methoxybenzyl carbonyl, t-butyloxycarbonyl, 9-fluorenylmethyloxycarbonyl, acetyl, trifluoroacetyl, benzoyl, benzyl, carbamate, 3,4-dimethoxybenzyl, p-methoxybenzyl, tosyl, trichloroethyl chloroformate, (4-nitrophenyl) sulfonyl, methyl, ethyl, propyl, n-butyl, t-butyl, succinimide, 2,6-dimethylphenol, 2,6-diisopropylphenol, 2,6-di-tert-butylphenol, trimethylsilyl, allyl, 1,1-dimethylallyl, 2,2,2-trifluoro ethyl, phenyl, and 4-methoxybenzyl.

6. The process of claim 5 wherein R is t-butyloxycarbonyl.

7. The process of claim 1 wherein each Y is independently selected from Cl, Br, and I.

8. The process of claim 4 wherein each Y is Cl.

9. The process of claim 1 wherein X is selected from Cl, Br, and I.

10. The process of claim 9 wherein X is Cl.

11. The process of claim 1 wherein the compound of Formula VI is the compound

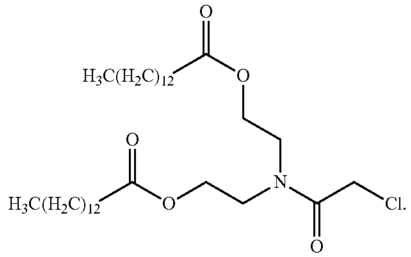

12. The process of claim 1, wherein the compound of Formula I is the compound

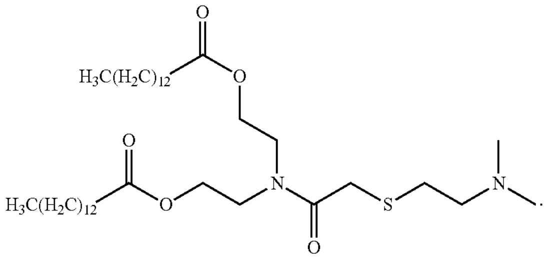

13. The process of claim 1 wherein, the yield of a) is at least about 80%.

14. The process of claim 1, wherein the compound of Formula I is produced in at least about 60% yield from the compound of Formula II.

15. The process of claim 1 wherein a compound of Formula VIII:

VIII

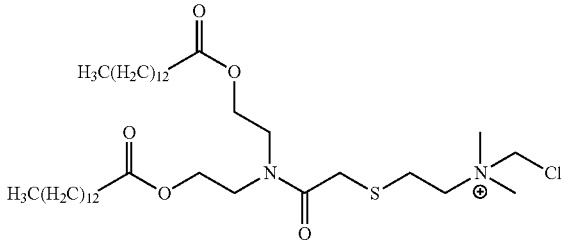

is present in the product from step d) in a concentration of less than 100 ppm.

16. The process of claim 1 wherein the compound of Formula VII is isolated as a crystalline solid.

* * * * *